US006667058B1

(12) United States Patent
Goede et al.

(10) Patent No.: US 6,667,058 B1
(45) Date of Patent: *Dec. 23, 2003

(54) ORAL FORMS OF ADMINISTRATION CONTAINING SOLID FLUPIRTINE WITH CONTROLLED RELEASE OF ACTIVE SUBSTANCE

(75) Inventors: Joachim Goede, Hanau (DE); Helmut Hettche, Dietzenbach (DE); Helmut Momberger, Marburg (DE); Jürgen Engel, Alzenau (DE); Michael Lobisch, Ober-Ramstadt (DE)

(73) Assignee: Viatris GmbH & Co. KG, Frankfurt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 702 days.

(21) Appl. No.: 08/212,578

(22) Filed: Mar. 17, 1994

(30) Foreign Application Priority Data

Mar. 18, 1993 (DE) ............................................ 43 08 572
Jun. 14, 1993 (DE) ............................................ 43 19 649

(51) Int. Cl.⁷ ............................ A61K 9/08; A61K 9/14; A61K 9/22; A61K 9/48; A61K 31/44; A61P 25/04
(52) U.S. Cl. ...................... 424/473; 424/78.1; 424/468; 424/502; 424/436; 424/457; 424/423; 514/357

(58) Field of Search ................................. 424/473, 423, 424/435–36, 78.1, 468, 484, 502, 471–72, 457; 514/357

(56) References Cited

U.S. PATENT DOCUMENTS

| | | | | |
|---|---|---|---|---|
| 3,896,108 A | * | 7/1975 | Klug | 424/495 |
| 4,728,513 A | * | 3/1988 | Ventouras | 424/495 |
| 4,748,023 A | * | 5/1988 | Tamas et al. | 424/495 |
| 4,959,219 A | * | 9/1990 | Chow et al. | 424/498 |
| 5,162,346 A | * | 11/1992 | Lobisch et al. | 514/356 |
| 5,229,131 A | * | 7/1993 | Amidon et al. | 424/451 |
| 5,238,686 A | * | 8/1993 | Eichel et al. | 424/495 |

* cited by examiner

*Primary Examiner*—Edward J. Webman
(74) *Attorney, Agent, or Firm*—Vanable LLP; Ann S. Hobbs

(57) ABSTRACT

Pharmaceutical dosage units containing flupirtine or a pharmaceutically acceptable salt of flupirtine with controlled release of active substance using a delayed-action or controlled-release component. There are 0.001 to 20 parts delayed-action component for each part by weight flupirtine (calculated as the base) and the release rate of flupirtine is between 5 and 300 mg per hour. In some cases, the dosage units may also contain a rapidly releasing component of flupirtine or of one of its salts. The dosage units reduce the sedative effect of flupirtine.

14 Claims, No Drawings

ORAL FORMS OF ADMINISTRATION CONTAINING SOLID FLUPIRTINE WITH CONTROLLED RELEASE OF ACTIVE SUBSTANCE

The present invention relates to pharmaceutical dosage forms containing flupirtine with controlled release of the active ingredient.

BACKGROUND OF THE INVENTION

Flupirtine is a pharmaceutically active substance having the formula:

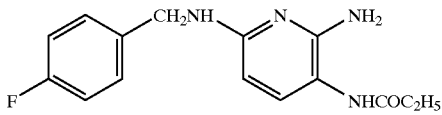

Flupirtine is useful as an analgesic. However, it sometimes causes a sedative side-effect.

SUMMARY OF THE INVENTION

The object of the present invention is to provide a solid dosage form of the pharmaceutically active substance flupirtine in which the sedative side effects of the flupirtine are largely or totally suppressed. A further object of the invention is to provide a solid dosage form of flupirtine which is useful for patients who require therapy with an analgesic which formulation does not have to be taken as frequently as in the case of conventional formulations.

The invention is particularly advantageous for patients with severe pain, e.g. tumor patients, who find the less frequent administration of drugs as well as longer duration of action to be advantageous, especially in the case of night pain. A further advantage of the invention is that the amount of active substance to be used daily takes strain off the body, especially the liver.

These and other objects are achieved by means of a pharmaceutical dosage form or pharmaceutical composition comprising or consisting essentially of flupirtine as the active substance and containing, in addition to customary adjuvants and additives, a delayed-action or controlled-release component. The composition is formulated so that the active substance flupirtine or its pharmaceutically-acceptable salts is/are released in a controlled manner and is present in an amount of 1 part by weight flupirtine, relative to the base, per 0.001 to 20 parts by weight delayed-action or controlled-release component and that the release is from 5 to 300 mg, e.g. 10 to 100 mg or also 20 to 60 mg flupirtine/hour. The pharmaceutical dosage unit may be formulated for oral administration and contain 50 to 600 mg flupirtine active substance, for parenteral use and contain 50 to 500 mg flupirtine active substance or for dermal use and contain 5 to 5000 mg flupirtine active substance.

This pharmaceutical composition with controlled release of the active substance can also be combined with an additional amount of flupirtine or of one of its pharmaceutically acceptable salts, which additional amount is formulated without the addition of delayed-action component and is rapidly released, that is, within 10 to 20 minutes. This additional amount can provide an initial phase of treatment assuring a rapid commencement of the action of the dosage form. In this manner, such a form of administration can bring about a rapidly commencing and long-lasting action, which is desirable for pain-killers. The amount of the initial phase flupirtine, i.e., without controlled-release component, in proportion to the amount of flupirtine which is released in a controlled manner, is in this instance 2:1 to 1:9 (amounts by weight in each instance, based on the amount of flupirtine base).

As indicated above, the flupirtine can be present as the free base or as a salt. Suitable salts are e.g. chloride, maleate, D-gluconate. If the flupirtine is present in the form of a salt, the amount of flupirtine, indicated above and calculated as the base, is increased corresponding to the greater molecular weight of the salt. The amounts in this description in the "flupirtine" indication always refers to the base and should be converted, upon the presence of a salt, in accordance with the increased molecular weight.

A further object of the invention is to provide a method for preparing a pharmaceutical composition of flupirtine which achieves controlled release of active substance, the method comprising introducing the active substance into customary adjuvants and additives and a delayed-action or controlled-release component which method is characterized in that flupirtine or its physiologically compatible salts are used in a ratio of 1 part by weight flupirtine, calculated as the base, per 0.001 to 20 parts by weight delayed-action component as active substance to be released in a controlled manner and that the release rate is adjusted to the range of 5 to 300 mg flupirtine/hour.

If the active substance flupirtine is placed in a form of administration which releases the active substance over a fairly long time period (and therewith brings about a "delaying" of the effect of the active substance), the side effect of tiredness is no longer detected in persons treated with this form of administration.

The subject matter of the invention is therefore constituted by solid forms of administration with a controlled release of the active substance flupirtine or pharmaceutically salts of flupirtine. Further subject matter of the invention comprises a method of preparing a dosage form which provides controlled release of the active substance flupirtine or of pharmaceutically acceptable salts of flupirtine.

The determination of the release rate of flupirtine within the limits indicated on above is carried out in an aqueous solution with pH 1 or 6.8. The pH's are adjusted by means of the addition of acid or by the addition of a customary buffer, e.g. a phosphate buffer. The method is described in the USP XXII, Jan. 1, 1990, pp. 1578–1579.

The following are potential examples of forms of administration: Tablets, film tablets, hard-gelatin capsules, soft-gelatin capsules, pellets, granulates, coated tablets, suppositories, microcapsules, aqueous or oily suspensions, oily solutions.

The controlled-release compositions of the invention can be obtained as follows:

1. By binding flupirtine to physiologically compatible cation exchangers. The following can be used, for example, as such cation exchangers: Acrylic and methacrylic resins with exchangeable proton, acid groups: COO, e.g. Amberlite® IRP-64 polystyrene resins with exchangeable Na, acid groups: $SO_3$, e.g. Amberlite® IRP-69.

The ion exchangers are acidic ion exchangers. The maximum ratio of flupirtine : ion exchanger is approximately 1:1 and the minimum ratio is approximately 1 part by eight active substance per 800 parts ion exchange resin. It is preferable to use 1 to 400 parts by weight ion exchanger, quite especially 1 to 100 parts by weight ion exchanger per 1 part by weight active substance.

The binding of the flupirtine takes place by allowing a solution of flupirtine to run through a bed of the ion exchanger in a column or the ion exchanger is suspended in a solution of flupirtine, filtered off after agitation and washed. The charged ion exchanger is dried at temperatures of up to approximately 50° C. The charged ion-exchanger particles are also preferably provided with a casing, as is described e.g. in U.S. Pat. No. 4,221,776. An advantage of the additional casing resides in the fact that the release rate of the active substance can be varied and influenced by the selection of the casing material. The drying of the charged ion-exchanger particles provided with casing can take place with warm air of 70° C. to 90° C.

The charged ion-exchanger particles can be filled into hard-gelatin capsules or be prepared with the aid of water and thickening agents, flavoring substances, stabilizing substances and preservatives as a suspension as form of administration.

2. The encasing of active-substance particles, granulate- or pellet grains or of tablets containing flupirtine with coatings of the following substances, which casing substances can also be used in a mixture: Hydroxypropylmethyl cellulose phthalate or -acetate succinate; cellulose-, starch- as well as polyvinyl acetate phthalate; carboxymethyl cellulose; polyvinyl acetate; methyl cellulose phthalate, methyl cellulose succinate, methyl cellulose phthalate succinate as well as methyl cellulose phthalicacid semi-ester; zein; ethyl cellulose as well as ethyl cellulose succinate; shellac; gluten; ethylcarboxyethyl cellulose; ethacrylate-maleic-acid anhydride copolymer; maleic-acid anhydride vinylmethyl ether copolymer; styrene-maleic-acid copolymers; 2-ethyl-hexyl-acrylate-maleic-acid anhydride; crotonic-acid vinyl acetate copolymer; glutamic-acid/glutamic-acid ester copolymer; carboxymethylethyl cellulose glycerol monooctanoate; cellulose acetate succinate; polyarginine; fat, oils, waxes, fatty alcohols; anionic polymers of methacrylic acid and methacrylic-acid esters (Eudragit®L, Eudragit®S); copolymers of acrylic and methacrylic-acid esters with a low content of trimethyl ammonium methacrylate (Eudragit®RL, Eudragit®RS), copolymer of acrylic acid, methacrylic acid as well as its esters (ratio of the free carboxyl groups to the ester groups e.g. 1:1) (Eudragite®L 30 D), copolymer of acrylic-acid ethyl- and methacrylic-acid methyl ester (Eudragit®NE 30 D).

The substances cited can additionally contain conventional softeners (e.g. dibutyl sebacate, citric and tartaric-acid esters, glycerol and glycerol esters, phthalic-acid esters and similar substances) and, moreover, the addition of water-soluble substances such as polyethylene glycols, polyvinyl pyrrolidone, copolymer of polyvinyl pyrrolidone and polyvinyl acetate, hydroxypropyl cellulose, hydroxypropyl methyl cellulose. The addition of solids such as talcum and/or magnesium stearate in the casing is also possible.

The pellet grains, granulate grains or tablets can also contain worked-in additives of organic acids (such as e.g. citric acid, tartaric acid, maleic, fumaric, ascorbic acid).

The encasing takes place by spraying on solutions in organic solvents or suspensions of the cited substances in organic solvents or water and even further adjuvants can be added in order to optimize their ability to be processed such as e.g. surface-active agents and pigments.

The spraying on takes place e.g. in a coating pan or in perforated pans or in an air-suspension method (e.g. Glatt fluid-bed system WLSD5). The encasing can also take place by coagulating aqueous dispersions of the above-named substances in that the active substance is mixed with the dispersion and the water removed by drying.

Coated active-substance particles and coated granulates can be pressed to form tablets, coated pellets filled into hard-gelatin capsules or pressed, after the addition of further substances, to tablets.

When coating active-substance particles or granulates containing the active-substance particles, it is customary to use more casing substance than in the case of pellets since the surface which must be covered is considerably greater than in the case of pellets.

0.001 to 20 parts by weight casing substance can be used per 1 part by weight active substance. A weight ratio of 1 part active substance and 0.005 to 10 parts by weight casing material is preferred and 0.01 to 5 parts by weight casing material for each part by weight active substance is quite especially preferred. The application of the casing substances takes place at elevated temperature, preferably in a current of air, supply-air temperature e.g. 70 to 90° C.; temperature of the exhaust air e.g. up to 40° C.

3. The encasing of compacts, tablets and granulates containing flupirtine and one or more osmotically active substances (e.g. mannitol, sorbitol) with a semipermeable membrane, e.g. consisting of 70 to 90 % by weight cellulose acetate and hydroxypropylmethyl cellulose (30 to 10 % by weight).

The following can also be considered as potential osmotically active substances: Organic and inorganic compounds or soluble substances which generate an osmotic pressure gradient vis-a-vis the external liquid via the semipermeable wall. Osmotically active agents or osmotically active compounds comprise magnesium sulfate, magnesium chloride, sodium chloride, lithium chloride, potassium sulfate, potassium hydrogen phosphate, urea, saccharose and the like. Further osmotically active agents are known from U.S. Pat. Nos. 3,854,770; 4,077,407 and 4,235,236.

The following, for example, can be considered as potential semipermeable materials which are known as polymers for osmosis and reverse osmosis: Cellulose acylate, cellulose diacylate, cellulose triacylate, cellulose acetate, cellulose diacetate, cellulose triacetate, β-glucan acetate, acetaldehyde dimethyl acetate, cellulose acetate ethyl carbamate, polyamide, polyurethane, sulfonated polystyrene, cellulose acetate phthalate, cellulose acetate methyl carbamate, cellulose acetate succinate, cellulose acetate dimethyl amino acetate, cellulose acetate chloroacetate, cellulose dipalmitate, cellulose dioctanoate, cellulose dicaprylate, cellulose dipentanate, cellulose acetate valerate, cellulose acetate-p-toluene sulfonate, cellulose acetate butyrate, ethyl cellulose, selectively permeable polymers formed by means of the common precipitation of a polycation and of a polyanion as indicated in U.S. Pat. Nos. 3,173,876; 3,276, 586; 3,541,005; 3,541,006 and 20 3,546,142. Such encasings in semipermeable membranes can also take place e.g. in accordance with published German Patent Applications DE-A 33 10 081 (U.S. Pat. No. 4,449,983) or DE-A-33 10 096 (U.S. Pat. No. 4,455,143).

The amount of osmotically active substance can be, for each part by weight flupirtine, from 1 to 20 parts by weight, preferably 2 to 6 and quite especially preferably 4 to 5 parts by weight. The casing substances are applied in such an amount that the semipermeable membrane is 50 to 500 μm thick, preferably 100 to 300 μm thick.

The processing of the active substance and of the osmotically active substances can take place between room temperature and 80° C. In order to adjust the release rate, the matter is dried e.g. at 70–90° C. supply-air temperature.

If required, the semipermeable membrane can also contain a microporous layer or microporous substances can be worked in (cf. German Offenlegungsschrift 33 10 081 (U.S. Pat. No. 4,455,143), e.g. pages 7–17 of the German text).

Materials suitable for producing the microporous layer comprise e.g. polycarbonates of linear polyesters of carbonic acid in which carbonate groups recur in the polymer chain, microporous materials produced by phosgenation of a dihydroxy aromatic compound such as bisphenol, a microporous polyvinyl chloride, microporous polyamides such as polyhexamethyl adipic acid amide (nylon 66), microporous modacrylic polymers including those formed from polyvinyl chloride and acrylonitrile, microporous styrene acrylic monomers and their copolymers, porous polysulfones characterized by the presence of diphenylene sulfone groups in a linear chain, halogenated or of an anhydride with an alkylene polyol, polyalkyl sulfides, phenolic polymers, polyesters, microporous polysaccharides with substituted anhydro glucose units exhibiting a decreasing permeability for water and biological liquids, asymmetric porous polymers, cross-linked olefin polymers, hydrophobic or hydrophilic microporous homopolymers, copolymers or interpolymers with a reduced density as well as materials described in U.S. Pat. Nos. 3,595,752; 3,643,178; 3,654,066; 3,709,774; 3,718,532; 3,803,601; 3,852,224; 3,852,388 and 3,853,601, in British Patent 1,126,849 and in Chemical Abstracts, vol. 71, 427F and 22573F (1969).

Further microporous materials for producing the microporous layer comprise polyurethanes, cross-linked chain-lengthened polyurethanes, polyimides, polybenzimidazoles, collodium, regenerated proteins, semisolid cross-linked polyvinyl pyrrolidone, microporous materials produced by diffusion from polyvalent cations in polyelectrolyte sols, microporous derivatives of polystyrene such as sodium polystyrene sulfonate, polyvinyl benzyl trimethyl ammonium chloride, microporous cellulose acylates and similar microporous polymers which are known from U.S. Pat. Nos. 3,524,753; 3,565,259; 3,276,589; 3,541,055; 3,541,006; 3,546142; 3,615,024; 3,646,178 and 3,852,224.

The pore-forming materials suitable for producing the microporous layer comprise solids and pore-forming liquids. The expression "pore-forming material", as it is used here, also includes substances which form micropassages and the removal of the pore-forming materials can result in both types. The expression "pore-forming liquids" includes semisolid and viscous liquids in the framework of this description. The pore-forming materials can be inorganic or organic and the layer-forming polymer generally contains 5 to 70% by weight pore-forming materials, especially 20 to 50% by weight. The expression "pore-forming material" comprises, both for solids and for liquids, substances which can be dissolved out of, extracted or leached out of the precursor of the microporous membrane by the liquid present in the application environment with formation of an effective, open-cell, microporous layer. The pore-forming solids have a particle size of approximately 0.1 to 200 µm and comprise alkali salts such as lithium carbonate, sodium chloride, sodium bromide, potassium chloride, potassium sulfate, potassium phosphate, sodium acetate, sodium citrate and the like. Organic compounds such as saccharides including the sugars saccharose, glucose, fructose, mannitol, mannose, galactose, sorbitol and the like. Soluble polymers such as carbo waxes, Carbopol® and the like can also be used. The pore-forming materials also include diols, polyols, polyvalent alcohols, polyalkylene glycols, polyglycols, poly(α-ω)-alkylene diols and the like.

4. The embedding of flupirtine and flupirtine salts or the binding to the following substances or mixtures of these substances:

Digestible fats, e.g. triglycerides of saturated fatty acids $C_8H_{16}O_2$ to $C_{18}H_{36}O_2$ and their mixtures, peanut oil and hydrated peanut oil, castor oil and hydrated castor oil, olive oil, sesame oil, cottonseed oil and hydrated cottonseed oil, corn oil, wheat germ oil, sunflower seed oil, cod liver oil, mixtures of mono-, di-, triesters of palmitic and of stearic acid with glycerol, glycerol trioleate, diglycol stearate, stearic acid, metal salts of fatty acids, especially alkaline-earth salts of fatty acids, e.g. magnesium stearate.

Indigestible fats and fat-like substances, e.g. esters of aliphatic saturated or unsaturated fatty acids (2 to 22 carbon atoms, especially 10 to 18 carbon atoms) with monovalent aliphatic alcohols (1 to 20 carbon atoms), carnauba wax, beeswax, fatty alcohols (straight-chain or branched-chain) with the empirical formula $C_8H_7OH$ to $C_{30}H_{61}OH$, especially $C_{12}H_{25}OH$ to $C_{24}H_{49}OH$.

Polymers such as polyvinyl alcohol, polyvinyl chloride, polyacrylic acid (Carbopol®); anionic polymers of methacrylic acid and methacrylic acid esters (Eudragit®L, Eudragit®S), acrylic and methacrylic acid ester copolymers with trimethyl ammonium methacrylate (Eudragit®RL, Eudragit®RS) copolymer from acrylic acid ethyl and methacrylic acid methyl esters (Eudragit®NE 30 D), as well as from acrylic acid, methacrylic acid as well as their esters (ratio of the free carboxyl groups to the ester groups 1:1) (Eudragito®- L 30 D), polyethylene, polyglycolic acid, polyhydroxy butyric acid, polylactic acid, copolymers of lactic acid and glycolic acid (producer: Boehringer Ingelheim), copolymers of lactic acid and ethylene oxide, copolymers of glycolic acid and ethylene oxide, copolymers of lactic acid and hydroxy butyric acid, hydroxypropylmethyl cellulose phthalate or acetate succinate; cellulose acetate phthalate, starch acetate phthalate as well as polyvinyl acetate phthalate; carboxymethyl cellulose; methyl cellulose phthalate, -succinate, -phthalate succinate, methyl cellulose phthalic acid semi-ester; zein; ethyl cellulose; shellac, gluten; ethyl carboxyethyl cellulose; ethyl acrylate-maleic-acid anhydride copolymer; maleic-acid anhydride vinylmethyl ether copolymer; styrene-maleic-acid copolymers; 2-ethyl-hexyl-acrylate-maleic-acid anhydride; crotonic-acid vinyl acetate copolymer; glutamic acid/glutamic-acid ester copolymer; carboxymethylethyl cellulose glycerol monooctanoate; cellulose acetate succinate; polyarginine; cross-linked alginate; cross-linked gelatins;

Swellable substances such as methyl cellulose, hydroxypropyl cellulose, hydroxypropylmethyl cellulose (Pharmacoat, Methocel E=propylene glycolic ether of methyl cellulose), alginic acid and its salts (Na-, Ca salt, also mixtures of sodium alginate and calcium salts, e.g. $CaHPO_4$), starch, carboxymethyl starch, carboxymethyl cellulose and its salts (e.g. Na salt), galactomannan, gum arabic, karaya gum, gum ghatti, agar-agar, carrageen, xanthan gum, guar gum and its derivatives, carob-seed meal, propylene glycol alginate, pectin, tragacanth.

In these delayed-action components 0.001 to 20 parts by weight delayed-action component, preferably 0.5 to 10 parts by weight and quite especially preferably 1.0 to 5 parts by weight are used for each part by weight flupirtine. The production of these preparations takes place at temperatures between 18° C. and 80° C.

The production of this form of administration can take place:

a) By dissolving or dispersing flupirtine or its salts in the cited fats or fat-like substances or mixtures thereof, even with melting of the cited substances and subsequent re-cooling, comminution, possible addition of further substances such as e.g. the above-mentioned substances which are water-soluble or swellable in water and pressing into tablets. The cooling off of the melt and comminution can also be combined in one step in that the melt is dispersed in cold water or is subjected to a spray drying. When the above-mentioned oils are used as retarding agent, flupirtine or its salt is dissolved or suspended in the oil and, if required, after the addition of up to 2% aluminum monostearate, filled into ampoules and subsequently sterilized or, if required, homogenized after the addition of flavoring substances and/or sedimentation retarders such as highly disperse silicon dioxide (e.g. Aerosilo) and dispensed into bottles;

b) By mixing flupirtine or its salts with the cited fats, polymers or swellable substances or mixtures of these substances, also with the use of heat, and pressing the mixtures, if required, after the addition of further adjuvants to tablets or forming to pellets;

c) By mixing flupirtine or its salts with solutions of the cited fats or polymers in water or organic solvents such as e.g. ethanol, ethyl acetate, acetone or isopropanol, if required, mixing with carrier materials such as cellulose, as well as subsequent evaporation of the solvent and mixing the embedded active-substance obtained in this way with further adjuvants and processing to formed materials such as e.g. tablets or pellets;

d) By moistening a mixture of flupirtine or its salts and the cited swellable substances with organic solvents such as ethanol, ethyl acetate, acetone or isopropanol, if required, with the addition of binders such as polyvinyl pyrrolidone or copolymers of polyvinyl pyrrolidone and polyvinyl acetate, granulating the mixture obtained, subsequent drying, the addition of possibly further adjuvants and pressing the mixture to tablets;

e) By mixing flupirtine or its salts with a solution of natural or artificial resins such as shellac or polyvinyl acetate in polyethylene glycol with a molar weight of 200 to 1500, the possible addition of further adjuvants such as e.g. stearates or swellable substances and the encapsulation of the mass obtained in solid or hard-gelatin capsules.

In general, the production of the dosage units takes place in a known manner; in addition to the delayed-action components the known and customary pharmaceutical adjuvants as well as other customary carriers and diluting agents can be used. The adjuvants cited as delayed-action component can also perform other functions, e.g. as mold-release agents or as disintegrants.

Those substances can be considered as such carriers and adjuvants, for example, which are recommended or indicated in the following literature as adjuvants for pharmacy, cosmetics and related areas: Ullmanns Encyklopadie der technischen Chemie, vol 4 (1953), pp. 1 to 39; Journal of Pharmaceutical Sciences, vol 52 (1963), pp. 918 ff.; H.v. Czetsch-Lindenwald, Hilfsstoffe fur Pharmazie und angrenzende Gebiete; Pharm. Ind., No. 2, 1961, pp. 72 ff.; Dr. H. P. Fiedler, Lexikon der Hilfsstoffe für Pharmazie, Kosmetik und angrenzende Gebiete, 3d edition, Editor Cantor, Aulendorf in Wurttemberg.

Examples of customary adjuvants, carriers and diluting agents are gelatins, natural sugars such as cane sugar or lactose, lecithin, pectin, starch (e.g. corn starch) as well as starch derivatives, cyclodextrins and cyclodextrin derivatives, polyvinyl pyrrolidone, gelatins, gum arabic, alginic acid, tylose, talcum, lycopodium, silica (e.g. colloidal), levulose, tragacanth, sodium chloride, stearates, magnesium salts and calcium salts of fatty acids with 12 to 22 carbon atoms, especially of the saturated ones (e.g. stearates), polyethylene glycol with an average molecular weight between 200 and 20,000, preferably between 200 and 5,000, especially between 200 and 1,000 or their mixtures and/or polymers of vinyl pyrrolidone and/or mixed polymers of vinyl pyrrolidone and vinyl. acetate. Esters of aliphatic, saturated or unsaturated fatty acids (2 to 22 carbon atoms, especially 10 to 18 carbon atoms) with monovalent, aliphatic alcohols (1 to 20 carbon atoms) or polyvalent alcohols such as glycols, glycerol, diethylene glycol, pentaerythritol, sorbitan, mannitol, etc., which can also be etherified, if required, benzyl benzoate, dioxolanes, glycerol formals, tetrahydrofurfuryl alcohol, polyglycol ether with $C_1$ to $C_{12}$ alcohols, dimethyl acetamide, lactamides, lactates, ethyl carbonates, silicones (especially polydimethyl siloxanes of average viscosity), calcium carbonate, sodium carbonate, calcium phosphate, sodium phosphate, magnesium carbonate, gum arabic, alginic acid, stearates, fats and substances with a similar action.

In addition, the dosage units can contain surface-active substances. The following are named by way of examples: alkali soaps such as alkali salts of higher fatty acids (e.g. Na-palmitate, Na-stearate) or their derivatives (e.g. Na-ricinoleate sulfate ester); sulfonated compounds or sulfonated compounds which arise by means of the conversion of higher fatty alcohols with sulfuric acid or chlorosulfonic acid and are used e.g. as sodium salts (e.g. sodium lauryl sulfate, sodium cetyl sulfate, sodium stearyl sulfate, sodium cetyl sulfonate); salts of bile acids; saponines; quaternary ammonium compounds; partial fatty-acid esters of sorbitan; partial fatty-acid esters and fatty-acid esters of polyoxyethylene sorbitan; polyoxyethylene sorbitan ethers; polyoxyethylene fatty-acid esters; polyoxyethylene fatty alcohol ethers; fatty-acid esters of saccharose; fatty-acid esters of polyglycerol; proteins; lecithins.

The forms of administration can also contain celluloses, especially if compressed tablets are to be produced. The following are potential candidates: Purified cellulose (e.g. as commercial Elcema®) or microcrystalline cellulose, e.g. as is commercially marketed under the name Avicelo. However, other fillers with a binder function can also be used such as calcium hydrogen phosphate, lactose, starches (e.g. potato starch, corn starch, modified starches such as starch ST 1500/Colorcon), glucose, mannitol, saccharose. Moreover, the forms of administration can contain sedimentation retarders such as e.g. highly disperse silicas having a surface of 50 to 500 $m^2/g$ especially 100 to 400 $m^2/g$ (determined according to the BET method). They are commercially available, e.g. under the name of Aerosil®.

In addition, the use of form-separating agents in the dosage units can be logical. The following can be cited as such agents: Talcum or siliconized talcum, calcium- and magnesium stearate, stearic acid, paraffin, hydrogenated fats and oils, silicon-oil emulsion.

Substances can also be considered as further adjuvants which bring about, e.g., tablet fragmentation, (so-called disintegrants) such as: Cross-linked polyvinyl pyrrolidone, sodium carboxymethyl starch and ultraamylopectin.

For the production of solutions and suspensions, e.g., water or physiologically compatible organic solvents such as e.g. ethanol, 1,3-propylene glycol, polyglycols and their derivatives come into consideration. For injectable solutions or suspensions, e.g. non-toxic, parenterally compatible diluting agents or solvents such as e.g. water, 1,3-butane diol, ethanol, 1,3-propylene glycol, polyglycols in a mixture with water, Ringer's solution, isotonic solution of common salt can be considered.

Moreover, the addition of stabilizers, colorants, antioxidants and complexing agents (e.g. ethylenediamine tetraacetic acid) and the like is possible as well as the addition of acids such as citric acid, tartaric acid, maleic acid, fumaric acid.

The following, for example, can be used as antioxidants: Sodium metabisulfite, cysteine, ascorbic acid and its esters (e.g. -palmitate), flavonoids, bile acid, bileacid alkyl ester, butylhydroxy anisol, nordihydroguaiaretic acid, tocopherols as well as tocopherols+synergists (substances which bind heavy metals by complex formation, e.g. lecithin, ascorbic acid, citric acid phosphoric acid).

Possible preservatives are e.g. sorbic acid, phydroxybenzoic-acid esters (e.g. low-alkyl ester), benzoic acid, sodium benzoate, trichloroisobutyl alcohol, phenol, cresol, benzethonium chloride and formalin derivatives.

The following can be considered as plasticizers for casing substances: Citric- and tartaric-acid esters (acetyl triethyl-, acetyl-tributyl-, tributyl-, triethyl-citrate); glycerol and glycerol esters (glycerol diacetate, -triacetate, acetylated monoglycerides, castor oil); phthalic-acid esters (dibutyl-, diamyl-, diethyl-, dimethyl-, dipropyl-, D-(2-methoxy- or ethyoxyethyl)-phthalate, ethylphthalyl- and butylphthalylethyl- and butylglycolate); alcohols (propylene glycol, polyethylene glycol of different chain lengths), adipates (diethyl-, di(l-methoxy- or ethoxyethyl)adipate); benzophenone; diethyl- and dibutyl sebacate, -succinate, -tartrate; diethylene glycol dipropionate; ethylene glycol diacetate, -dibutyrate, -dipropionate; tributyl phosphate, tributyrin; polyethylene glycol sorbitan monooleate; sorbitan monooleate.

For applying the delayed-action components and/or casing substances, solvents can be used from the group of aqueous solvents, alcohols, ketones, esters, ethers, aliphatic hydrocarbons, halogenated solvents, for example, among others, acetone, diacetone alcohol, methanol, ethanol, isopropyl alcohol, butyl alcohol, methyl acetate, ethyl acetate, isopropyl acetate, n-butyl acetate, methylisobutyl ketone, methylpropyl ketone, n-hexane, ethyleneglycolmonoethyl ether, ethylene glycol monoethyl acetate, methylene dichloride, ethyl dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diethylene glycol dimethyl ether, water and their mixtures such as acetone and water, acetone and methanol, acetone and ethyl alcohol, methylene dichloride and methanol and ethylene dichloride and methanol as well as their mixtures. These solvents are removed again during the course of the encasing process.

Independently of the method of production, the forms of administration of the invention release the active substance flupirtine or its physiologically compatible salts at a release rate between 5 and 300 mg per hour to body fluids or pass into the latter.

Dosing indications always refer to flupirtine as base; if salts of flupirtine are used, a conversion in accordance with the molar weight should be made.

The contents of flupirtine in the dosage units of the invention are:

10 mg-3000 mg, preferably
20 mg-2000 mg
10 50 mg-1500 mg.

The individual doses cited can be used 1–5 times, preferably 1–3 times, especially 1–2 times daily.

In general, a release rate from a tablet or capsule of 20–30 mg flupirtine per hour desirable.

DETAILED DESCRIPTION OF PREFERRED EMBODIMENTS

The invention is illustrated by the following examples.

EXAMPLE 1

Tablets with 200 mg Flupirtine Maleate 40.0 kg flupirtine maleate are mixed with 30.0 kg polyacrylic acid (trade name: Carbopolo 934, Goodrich), 18 kg microcrystalline cellulose, 5 kg lactose monohydrate and 5 kg citric acid. The mixture is thoroughly moistened with 30.0 kg purified water. After the mass had been dried to a relative humidity of 20–30 % the mixture was ground and sieved by a sieve with a mesh size of 0.8 mm. Then, 7.0 kg microcrystalline cellulose, 3.4 kg lactose monohydrate, 0.6 kg highly disperse silicon dioxide and 1.0 kg magnesium stearate are mixed in. The mixture is pressed to tablets with a weight of 550 mg, a diameter of 10 mm and a radius of curvature of 8 mm.

The tablets can be provided, if required, with a coating of film which is soluble in gastric juice or permeable to gastric juice.

Each tablet contains 200 mg flupirtine maleate. The release is determined with apparatus 2 of USP XXII (release medium 500 ml 0.1 N HCl or phosphate buffer pH 6.8. Rotating speed of the paddle: 90 rpms). It amounts to:

| After | | Release medium |
|---|---|---|
| 1 hour: | 19% | |
| 2 hours: | 51% | 0.1 N HCl |
| 3 hours: | 75% | |
| 4 hours: | 88% | phosphate buffer |
| 5 hours: | 92% | pH 6.8 |

EXAMPLE 2

Capsules with 200 mg flupirtine maleate in the form of lacquered pellets 1000 g flupirtine maleate are mixed with 20 g highly disperse silica. The powder mixture is applied onto 1000 g neutral pellets with a diameter of 0.6–0.85 mm. For this, the neutral pellets are moistened with the part of a solution of 50 g of a copolymer with anionic character based on methacrylic acid and methyl methacrylate (trade name: Eudragit® L 100 / Rohm Pharma, Weiterstadt) as well as 50 g shellac in 900 g ethanol to 96% and powder mixture subsequently applied. After having dried, this operating procedure is repeated until the powder mixture has been completely applied.

For further processing, the fraction is used between 0.8 and 1.25 mm pellet diameter.

A solution of 0.8 g of a copolymer with anionic character based on methacrylic acid and methyl methacrylate (trade name: Eudragit® L 100 / Rohm Pharma, Weiterstadt) and 0.8 g shellac in 14.4 g ethanol 96% and 16 g talcum are applied in accordance with the method described above onto 400 g of the pellets produced in this manner.

The pellets obtained are filled at 442.7 mg into hardgelatin capsules. Each capsule contains 200 mg flupirtine maleate.

The release is determined as in Example 1. It is:

| After | | Release medium |
|---|---|---|
| 1 hour: | 43% | |
| 2 hours: | 56% | 0.1 N HCl |
| 4 hours: | 69% | phosphate buffer |
| 6 hours: | 85% | pH 6.8 |
| 8 hours: | 95% | |

EXAMPLE 3

Hard-gelatin Capsules with 20 mg Flupirtine Maleate of which 70 mg is with Rapid Release and 130 mg Delayed Release 470 g flupirtine maleate are moistened with a solution of 9 g copolyvidon (trade name: Kollidon VA 64 /BASF) in 100 g purified water. Water is added subsequently until a mass capable of granulation is produced. This mass is pressed through a sieve with a mesh size of 3 mm and subsequently dried. After having been sieved through a sieve with a mesh size of 1 mm, the granulate is mixed with 5 g magnesium stearate and 2.5 g highly-disperse silicon dioxide and filled at 72.5 mg into hard-gelatin capsules. In addition, 287.8 mg of the pellets from Example 2 are filled into these hard-gelatin capsules.

EXAMPLE 4

Two-layer Tablets with 100 mg Flupirtine Maleate of which 50 g is with Rapid release and 50 mg with Delayed Release 10 kg flupirtine maleate are mixed with 10 kg calcium hydrogen phosphate and moistened with an aqueous solution of 1 kg polyvinyl pyrrolidone (Kollidon 25/BASF) in 8 kg purified water. Water is added subsequently until a mass capable of granulation is produced. The mass is passed through a sieve with a mesh size of 3 mm and dried. After having been sieved through a sieve with a mesh size of 1 mm, 6.95 kg corn starch, 5 kg microcrystalline cellulose, 0.25 kg highly-disperse silicon dioxide and 0.6 kg magnesium stearate are mixed in.

The mixture obtained is pressed together with the pressed mixture obtained in Example 1 to two-layer tablets with a total weight of 306.5 mg. In these two-layer tablets one layer consists of 169 mg of the mixture obtained above and the other layer of 137.5 mg of the pressed mixture obtained in Example 1. As a result thereof each two-layer tablet contains 100 mg flupirtine maleate of which 50 mg is of the rapid release type and 50 mg of the delayed release type.

The two-layer tablets can be provided, in accordance with customary methods, with a coating of film which is soluble in gastric juice or is permeable to gastric juice.

What is claimed is:

1. A method of treating patients that require therapy with an analgesic such that sedative side effects of the analgesic are reduced comprising the administration of a pharmaceutical dosage unit comprising a pharmaceutically acceptable salt or a mixture thereof and a controlled release component, wherein 0.001 to 20 parts controlled release component are present for each part by weight flupirtine (calculated as flupirtine base).

2. The method according to claim 1 wherein in the pharmaceutical dosage unit the release rate of flupirtine is between 5 and 300 mg per hour, determined in accordance with the method of USP XXII with apparatus 2 in an aqueous test solution of pH 1.0 and/or pH 6.8.

3. The method according to claim 1 wherein the pharmaceutical dosage unit contains at least one pharmaceutically acceptable carrier.

4. The method according to claim 1 wherein in the pharmaceutical dosage unit the flupirtine a) is encased with one or more delayed-action components, or b) is bound to a cation exchanger, or c) is compounded with one or more osmotically active substances and encased with a semi-permeable membrane into which an aperture is bored, or d) is embedded in one or more substances from the group of digestible fats, or indigestible fats or fat-like substances, polymers or swelling substances.

5. The method according to claim 1 in which the dosage unit is formulated for oral administration and contains 50 to 600 mg of the flupirtine base or an equivalent amount of a pharmaceutically acceptable salt thereof.

6. The method according to claim 1 wherein the dosage unit is formulated for parenteral use and contains 50 to 500 mg flupirtine active substance.

7. The method according to claim 1 wherein the dosage unit is formulated for dermal use and contains 5 to 5000 mg flupirtine active substance.

8. The method according to claim 1 wherein the pharmaceutical dosage unit additionally comprises flupirtine rmulated for immediate release of active substance, the ratio of flupirtine formulated for controlled release and flupirtine formulated for immediate release being between 1 to 2 and 9 to 1.

9. The method according to claim 1 wherein the pharmaceutical dosage unit additionally comprises flupirtine formulated for immediate release of active substance, the ratio of flupirtine formulated for controlled release and flupirtine formulated for immediate release being between 1 to 2 and 9 to 1.

10. The method according to claim 3 wherein the pharmaceutical dosage unit additionally comprises flupirtine formulated for immediate release of active substance, the ratio of flupirtine formulated for controlled release and flupirtine formulated for immediate release being between 1 to 2 and 9 to 1.

11. The method according to claim 4 wherein the pharmaceutical dosage unit additionally comprises flupirtine formulated for immediate release of active substance, the ratio of flupirtine formulated for controlled release and flupirtine formulated for immediate release being between 1 to 2 and 9 to 1.

12. The method according to claim 5 wherein the pharmaceutical dosage unit additionally comprises flupirtine formulated for immediate release of active substance, the ratio of flupirtine formulated for controlled release and flupirtine formulated for immediate release being between 1 to 2 and 9 to 1.

13. The method according to claim 6 wherein the pharmaceutical dosage unit additionally comprises flupirtine formulated for immediate release of active substance, the ratio of flupirtine formulated for controlled release and flupirtine formulated for immediate release being between 1 to 2 and 9 to 1.

14. The method according to claim 7 wherein the pharmaceutical dosage unit additionally comprises flupirtine formulated for immediate release of active substance, the ratio of flupirtine formulated for controlled release and flupirtine formulated for immediate release being between 1 to 2 and 9 to 1.

* * * * *

UNITED STATES PATENT AND TRADEMARK OFFICE
CERTIFICATE OF CORRECTION

PATENT NO.       : 6,667,058 B1
APPLICATION NO.  : 08/212578
DATED            : December 23, 2003
INVENTOR(S)      : Joachim Goede et al.

It is certified that error appears in the above-identified patent and that said Letters Patent is hereby corrected as shown below:

Title page, under item [*] Notice: should read -- under 35 U.S.C. 154(b) by 0 days. --

Signed and Sealed this

Nineteenth Day of December, 2006

JON W. DUDAS
*Director of the United States Patent and Trademark Office*